US006170393B1

(12) United States Patent
Hook et al.

(10) Patent No.: US 6,170,393 B1
(45) Date of Patent: Jan. 9, 2001

(54) COMPLIANT EMBOSSER ASSEMBLY

(75) Inventors: Jeremy Frederic Hook, Greenville, NC (US); Dennis Allen DeHaan; Wilfried Maria Kollner, both of Cincinnati, OH (US)

(73) Assignee: The Procter & Gamble Company, Cincinnati, OH (US)

( * ) Notice: Under 35 U.S.C. 154(b), the term of this patent shall be extended for 0 days.

(21) Appl. No.: 09/083,147

(22) Filed: May 21, 1998

(51) Int. Cl.[7] .................................................. B31F 1/10
(52) U.S. Cl. ...................................................... 101/6; 101/5
(58) Field of Search ................................. 101/6, 5, 4, 3.1, 101/24, 23, 22; 492/49, 52, 51

(56) References Cited

U.S. PATENT DOCUMENTS

| | | | | |
|---|---|---|---|---|
| 1,528,956 | * | 3/1925 | Smith | 492/52 |
| 2,966,723 | * | 1/1961 | Swope | 101/148 |
| 3,264,978 | * | 8/1966 | Staley | 101/23 |
| 3,877,919 | * | 4/1975 | Shorr | 492/51 |
| 4,823,450 | * | 4/1989 | Ramisch et al. | 101/6 |
| 5,308,346 | * | 5/1994 | Sneller et al. | 604/385.2 |
| 5,411,463 | * | 5/1995 | Brookstein | 492/52 |
| 5,830,296 | * | 11/1998 | Emenaker et al. | 156/219 |

* cited by examiner

Primary Examiner—John S. Hilten
Assistant Examiner—Anthony H. Nguyen
(74) Attorney, Agent, or Firm—Ingrid N. Hickman; Jeffrey V. Bamber

(57) ABSTRACT

An apparatus for embossing a pattern into absorbent articles such as sanitary napkins, panty liners, diapers, and adult incontinence pads is disclosed. The apparatus for forming a pattern of embossments in an absorbent article comprises an embosser assembly having a patterned die roll and an anvil roll. In one embodiment, the anvil roll comprises a multi-layered structure, that comprises a metal hub, encircled by a compressible layer and enclosed by a sleeve which reduces machine dynamics, such as vibration, associated with the embossing apparatus and significantly improves the embossing line process and quality. The embosser assembly also has a mechanism for applying compressive pressure on the components of an absorbent article when the components are placed between the die roll and the anvil roll.

10 Claims, 5 Drawing Sheets

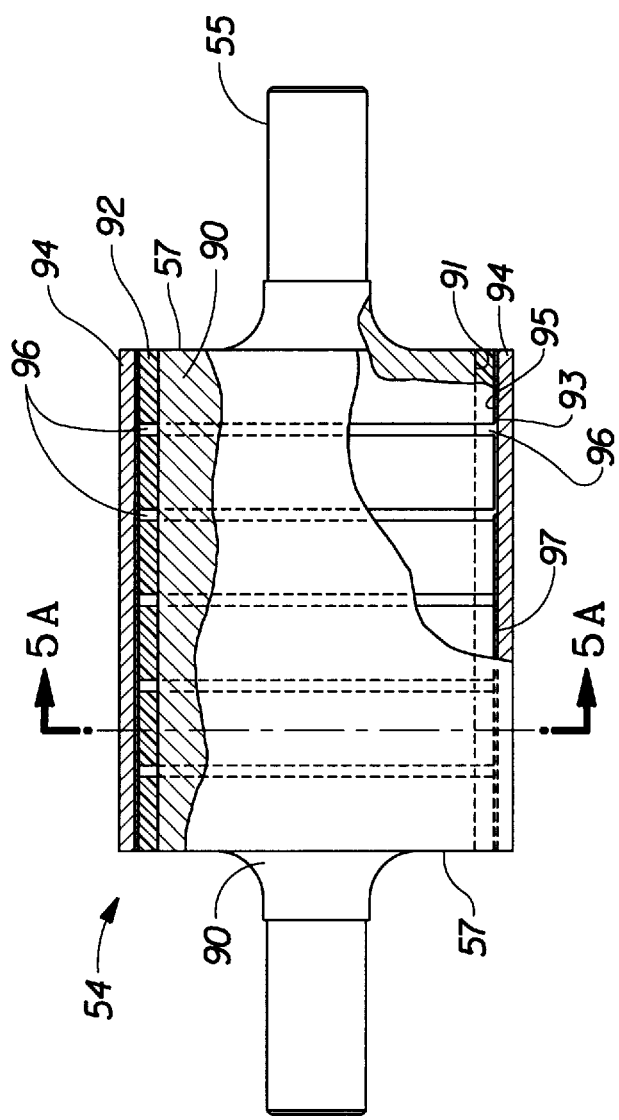
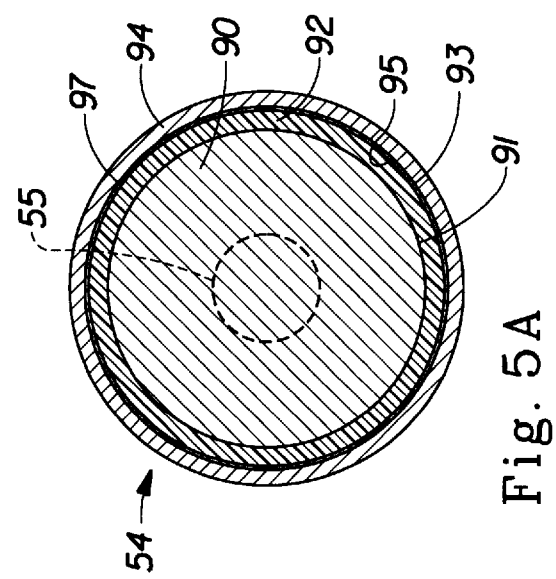
Fig. 5
Fig. 5A

COMPLIANT EMBOSSER ASSEMBLY

FIELD OF THE INVENTION

This invention relates to an apparatus for embossing a pattern into absorbent articles such as sanitary napkins, panty liners, and adult incontinence pads, more particularly the present invention relates to an anvil roll in an embosser assembly which reduces the machine dynamics such as vibration associated with the embossing apparatus and significantly improves the embossing line process and quality.

BACKGROUND OF THE INVENTION

All manner and variety of absorbent articles configured for the absorption of body fluids such as menses, urine, and feces are, of course, well known. Some particularly preferred absorbent articles are described in U.S. Pat. Nos. 5,308,346 and 5,234,422 issued to Sneller, et al., U.S. Pat. No. 5,460,623 entitled "Trisection Sanitary Napkin" issued to Emenaker, et al., and PCT Publication No. WO 94/10045, entitled "Sanitary Napkin Having Core Predisposed to a Convex Upward Configuration", published on Mar. 23, 1995 in the name of Letha M. Hines, et al.

The latter publication discloses providing the sanitary napkin with one or more lines of weakness that allow the sanitary napkin to bend in a preferred manner. The lines of weakness may be comprised of discrete embossment sites. In the manufacture of such absorbent articles, difficulties are often encountered with process reliability and embossment quality, particularly when the sanitary napkin is made in a high speed manufacturing operation. Machine dynamics, such as vibration, cause high stress concentrations, high wear, and fatigue which decrease the life of the embossing apparatus. An apparatus which increases the machine durability, reduces machines vibrations, creates a wide distribution of stress concentrations and provides a high degree of control over the registration of the embossing pattern is needed, particularly when the sanitary napkin or other absorbent articles are being made in a high speed manufacturing operation.

SUMMARY OF THE PRESENT INVENTION

The present invention is directed to an apparatus for embossing a pattern into absorbent articles such as sanitary napkins, panty liners, diapers, and adult incontinence pads which improves significantly the embossing line process and quality.

The apparatus for forming a pattern of embossments in an absorbent article comprises an embosser assembly having a patterned die roll and an anvil roll. The anvil roll comprises a multi-layered structure, that preferably comprises a hub, encircled by a compressible layer and enclosed by a sleeve. The multi-layered anvil roll reduces machine dynamics, such as vibration, associated with the embossing apparatus and significantly improves the embossing line process and quality. The embosser assembly also includes a mechanism for applying compressive pressure on the components of an absorbent article when the components are placed between the die roll and the anvil roll.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

FIG. 5 is a plan view of an anvil roll in the embosser assembly of the present invention and a cut away view of the anvil roll the in the embosser assembly with the outer sleeve removed.

FIG. 5A is a cross-sectional view of an anvil roll shown in FIG. 5 taken along line 5—5 in FIG. 5.

DETAILED DESCRIPTION OF THE INVENTION

This invention relates to an apparatus for embossing a pattern into absorbent articles such as sanitary napkins, panty liners, diapers, and adult incontinence pads which reduces the machine dynamics associated with an embossing apparatus and significantly improves the embossing line process and quality.

Figure 1:
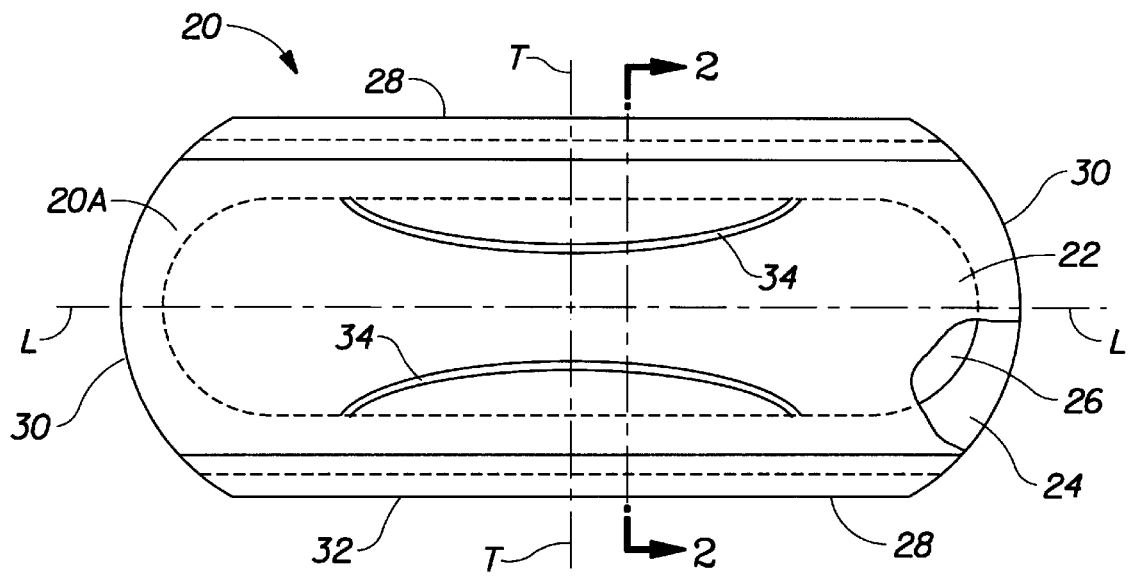
FIG. 1 is a top plan view of a sanitary napkin that was embossed with the apparatus of the present invention.
Figure 2:
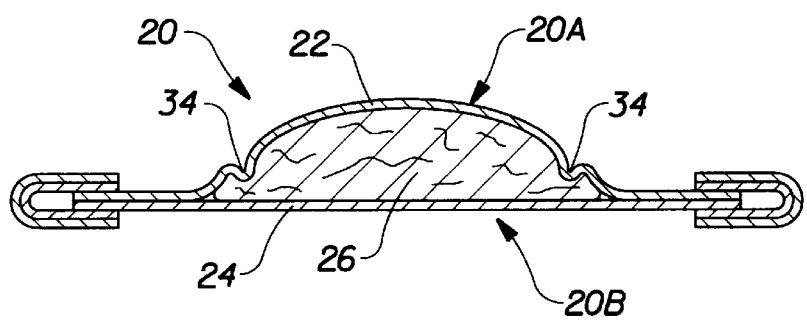
FIG. 2 is a cross-sectional view of the sanitary napkin shown in FIG. 1 taken along line 2—2 of FIG. 1.

FIG. 1 shows one embodiment of a disposable absorbent article, sanitary napkin 20 embossed using the process and apparatus of the present invention. The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. As shown in FIG. 2, the sanitary napkin 20 basically comprises a liquid pervious topsheet 22, a liquid impervious backsheet 24, and an absorbent core 26 positioned between the topsheet 22 and the backsheet 24.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction. The sanitary napkin 20 has two spaced apart longitudinal edges 28, two spaced apart transverse or end edges (or "ends") 30, which together form the periphery 32 of the sanitary napkin 20.

The embodiment of the sanitary napkin 20 shown in FIG. 1 is intended to be an example of a sanitary napkin having embossed channels similar to that described in U.S. Pat. Nos. 5,308,346 and 5,234,422 issued to Sneller et al. It should be understood that the sanitary napkin shown is merely one preferred embodiment, and that the present invention is not limited to making absorbent articles of the type or having the specific configuration shown in the drawings. The sanitary napkin can be provided with channel embossments 34 either in addition to, or as an alternative to another pattern of embossments.

Suitable materials for the various components of the sanitary napkin 20 shown in FIG. 1 are described in greater detail in U.S. Pat. Nos. 5,308,346 and 5,234,422 issued to Sneller, et al. and in the patent publications which are incorporated by reference herein. Preferably, the materials comprising at least the topsheet and backsheet are thermoplastic in order to bond these components at their edges. In a particularly preferred embodiment, the topsheet 22 comprises the apertures thermoplastic film sold on sanitary napkins by The Procter & Gamble Company of Cincinnati, Ohio, under the trademark DRI-WEAVE, which is manufactured under U.S. Pat. No. 4,342,314 issued to Radel, et al. on Aug. 3, 1982, and U.S. Pat. No. 4,463,045 issued to Ahr, et al. on Jul. 31, 1984. The absorbent core 26 may be manufactured in a wide variety of sizes and shapes as described in U.S. Pat. Nos. 5,308,346 and 5,234,422 issued to Sneller, et al. The backsheet 24 preferably comprises a polyethylene film. In an alternative embodiment in which the absorbent article comprises an ultra-thin sanitary napkin (shown in FIG. 4A), the absorbent core 26 comprises the absorbent core described in U.S. Pat. No. 5,460,623 issued to Emenaker, et al. In this case, the absorbent core 26 preferably comprises a tissue laminate with absorbent gelling material particles therebetween.

The sanitary napkin 20, as shown in FIG. 2, is assembled in a sandwich configuration in which the topsheet 22 and the backsheet 24 have length and width dimensions generally larger than those of the absorbent core 26 and encase the absorbent core 26. The embossed channels 34 are shown in FIG. 2 as being a region of the sanitary napkin 20 wherein preferably the channels 34 are impressed into both the topsheet 22 and the absorbent core 26.

Figure 3:
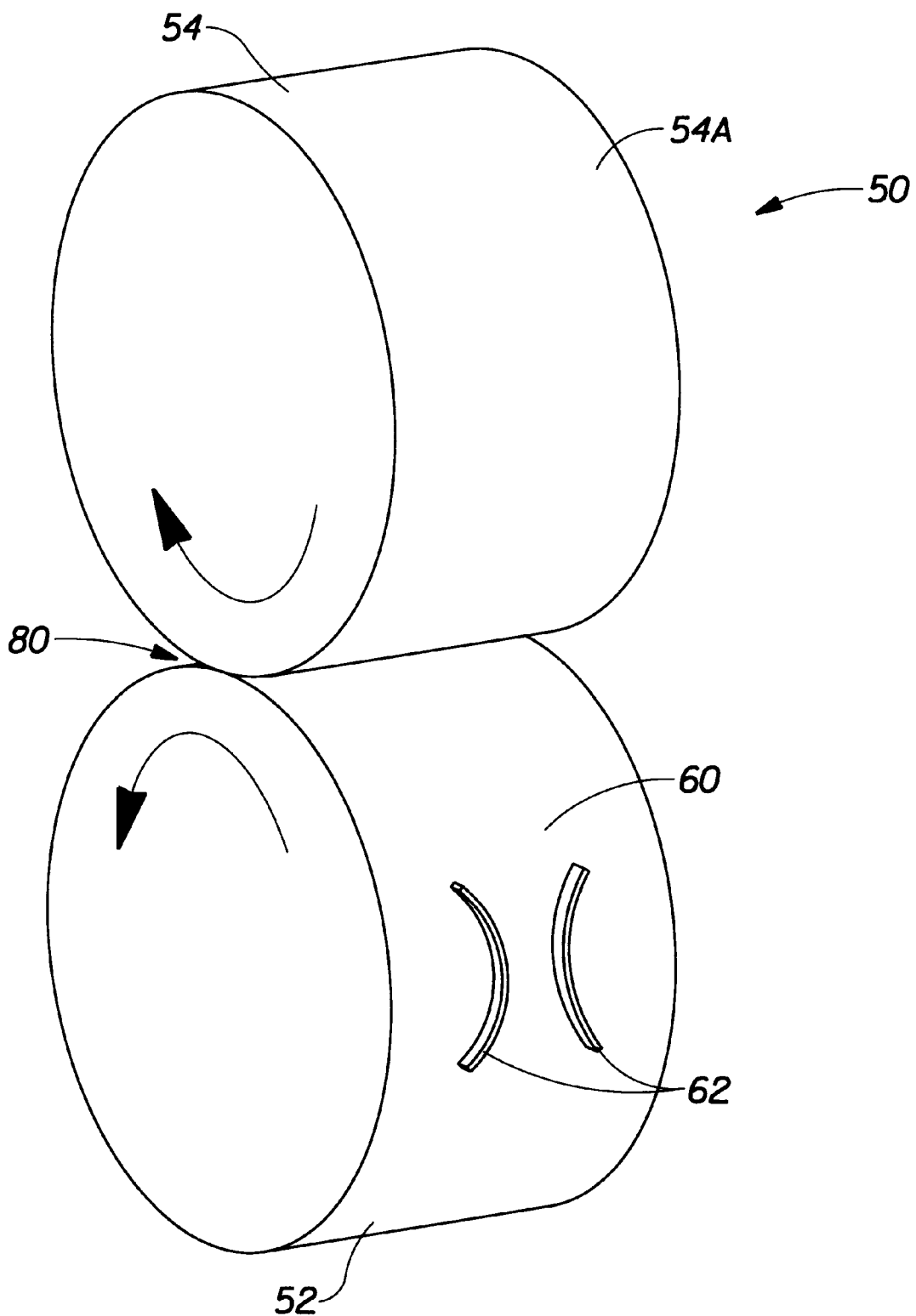
FIG. 3 is a perspective view of an anvil roll and die roll in a preferred embodiment of an embosser assembly of the present invention.
Figure 4:
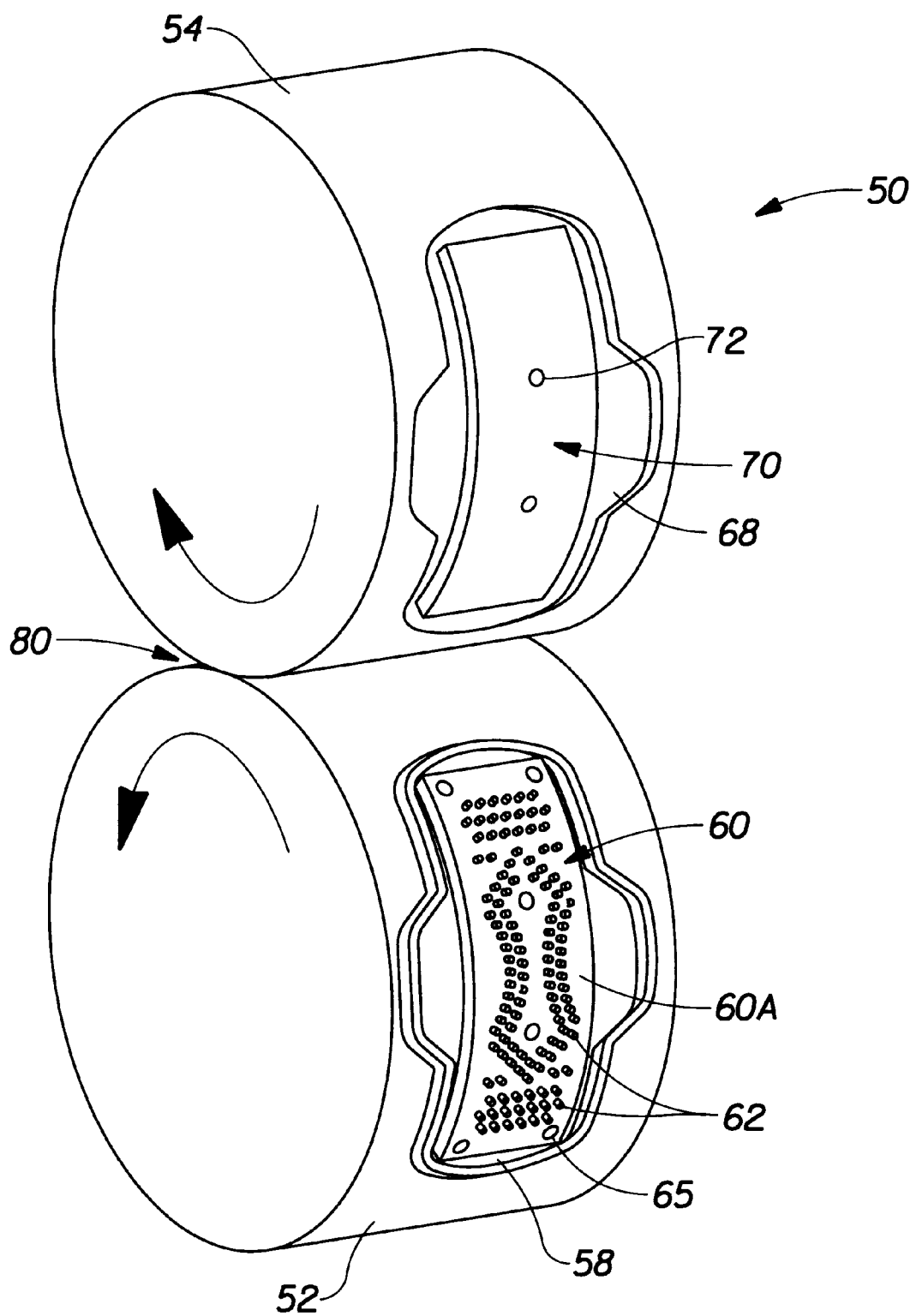
FIG. 4 is a perspective view of an anvil roll and die roll in an alternative embosser assembly of the present invention.
Figure 4A:
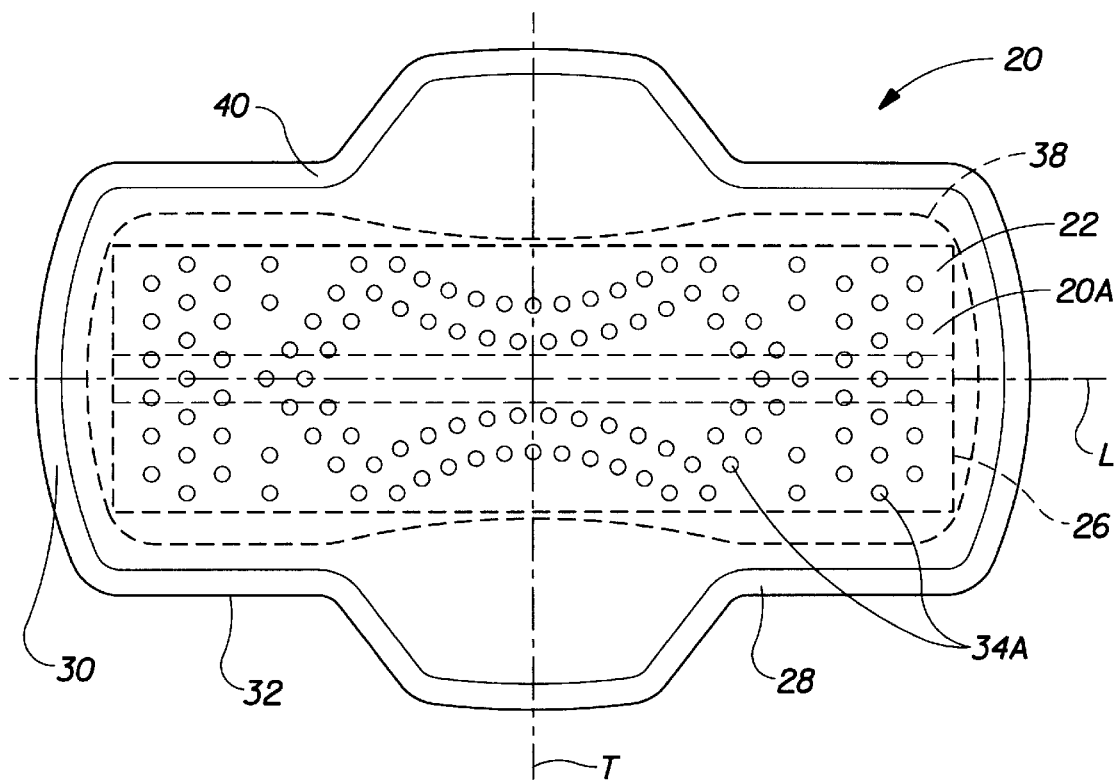
FIG. 4A is a top plan view of a sanitary napkin with embossments made using the apparatus of the present invention shown in FIG. 4.

FIG. 3 shows an embosser assembly 50 of the present invention used to make patterns of embossments such as embossments 34 on sanitary napkin 20 shown in FIG. 1. The embosser assembly 50 preferably comprises a die roll 52 and an anvil roll 54. The die roll 52 uses an embossing member 60 to form a pattern of embodiments. The embossments are formed by raised portions 62 which comprise part of the embossing member 60. The pattern of embossments may also be in the form of embossments 34A embossed into sanitary napkin 20 as shown in FIG. 4A, however the design and scope of the embossment pattern is not limited to the specific configurations shown in the figures. Any suitable pattern of embossments can be used. The embodiment of the sanitary napkin 20 shown in FIG. 4A is intended to be an example of a sanitary napkin similar to that described in U.S. Pat. No. 5,460,623 entitled "Trisection Sanitary Napkin" issued to Emenaker, et al. which is provided with a pattern of embossments 34A.

The die roll 52 and the anvil roll 54 are preferably both made of a hard metal, such as steel. In other embodiments, the anvil roll 54 can be provided with an anvil surface that comprises an insert or raised portions. The anvil roll 54 preferably has a substantially smooth surface.

In operation, the forces created during the embossing process occur in a step-function. The forces are the greatest when the anvil is in contact with a sanitary napkin imparting the embossed patterns and subside during the rotation of the anvil before the next sanitary napkin is embossed. Providing the compliant anvil roll with a substantially smooth surface minimizes non-uniform force distribution that would be caused by the substantial raised portions on the surface of the embossing member 60.

The embossing member 60 can be provided in any suitable form. The embossing member 60 can be in the form of a pattern directly on die roll 52 as shown in FIG. 3, or of a removable insert. In the embodiment shown in FIG. 4, the embossing member is in the form of a removable insert, embossing member 60. In FIG. 4 the die roll 52 has a recessed region 58 having a die insert or embossing member 60 therein. The embossing member 60 is preferably provided with a pair of bolt holes 65 and is bolted to the die roll 52 so that it is removable. This allows the embossing member 60 to be easily replaced when worn. It also provides the flexibility to change the pattern of embossments by replacing the removable insert with a different insert. The embossments 34 or 34A can also be eliminated from the absorbent article altogether by simply removing the embossing member 60.

The recessed region 58 allows the embosser assembly to accommodate the added thickness of the absorbent core in the central area of the sanitary napkin. The embossing member 60 comprises an embossing surface 60A with at least one raised portion 62 extending therefrom. The surface 60A of the embossing member 60 can have a plurality of raised portions 62 as seen in FIG. 4. The raised portions 62 will be used to form embossments 34 and 34A in the body surface 20A of the sanitary napkin 20. When the components of the absorbent article are fed into the nip 80 between the die roll 52 and the anvil roll 54, the raised portions 62 on the embossing surface 60A forms a pattern of embossments 34 and 34A into at least some of the components.

In operation, the components of the absorbent article (that is, the topsheet, backsheet, and absorbent core) are laid down on top of each other in the proper sequence, and if desired, at least some of these components are secured together at their faces. The components for the absorbent article are preferably provided in the form of a continuous web or laminate (except for the absorbent core and secondary topsheet which are preferably discontinuous patches or pieces). When the components are supplied to the embosser assembly shown in FIGS. 3 and 4, the components will be arranged in a laminate with the web of topsheet material facing downward.

The die roll 52 and anvil roll 54 are kept in the desired spaced apart relationship by a mechanism, such as a frame, for applying compressive pressure on the components of the sanitary napkin. The frame can be connected directly or indirectly to the die and anvil rolls and vertically aligns the die roll 52 and the anvil roll 54.

The die roll 52 and anvil roll 54 are preferably kept a certain distance apart to define a nip 80 between the rolls, through which the components of the sanitary napkin are fed. To form the particular ultra-thin sanitary napkin (shown in FIG. 4A), the distance between the die and anvil rolls is preferably less than or equal to about 0.025 inches (about 0.064 cm), and most preferably is about 0.015 inches (about 0.038 cm). The components are fed between the nip 80 which applies compressive pressure on the components of the absorbent article which is sufficient to form the embossments 34 therein, and in the embodiment shown in FIG. 4, also provide the perimeter seal 40 on sanitary napkin 20 shown in FIG. 4A.

The anvil roll 54 used in the present invention to reduce machine vibrations and to achieve a high degree of control over the registration of the embossing pattern 34 is shown in greater detail in FIGS. 5 and 5A. The anvil roll 54, shown in FIGS. 5 and 5A, preferably comprises an anvil shaft 55 and a multi-layered structure comprising a hub 90 that is connected to the anvil shaft 55; which is surrounded by a compliant and resilient intermediate element or layer 92 that is preferably made of an elastomeric material; and a less compliant, stronger, rigid sleeve or cover 94 that covers the intermediate element or layer 92 to reduce wear and provide durability. In the preferred embodiment, the anvil roll surface 54A preferably has a substantially smooth surface. The relationship of the components of the multi-layered structure are shown in FIG. 5A.

The preferred material for the hub 90 and anvil shaft 55 is steel, and more preferably stainless steel. Using a hard metal provides a stiff and rigid hub 90 and an anvil shaft 55. This enables the hub 90 and shaft 55 to withstand high loads with little deflection. The next layer is the intermediate element or layer 92. The intermediate element or layer 92 is preferably made of an elastomeric material that is molded onto the outer diameter 91 of the anvil hub 90. The intermediate layer 92 absorbs the stress and compressive forces that occur when the embosser assembly is in operation, lessening the vibration in the entire embosser assembly. The elastomeric material of the intermediate layer 92 and hardness of the hub 90 and anvil shaft 55 can vary depending upon the embodiment. Specifically for forming embossed channels, the intermediate layer material is preferably a polyurethane at hardness levels of 30 Shore A to 50 Shore A. The thickness of the intermediate layer 92 is preferably 0.08–3.0 inches (0.20–7.6 cm), more preferably 0.150–1.50 inches (0.38–3.80 cm), and most preferably 0.25–0.500 in (0.65–1.27 cm).

As seen in FIG. 5A, a thermoset or adhesive 97 is applied to the outer surface 93 of the molded intermediate layer 92 and to the inner surface 95 of the sleeve 94. The sleeve 94, made of a material like steel, is the final layer of material on the anvil roll 54. The thickness of the sleeve 94 is preferably 0.10–4.0 inches (0.25–10.2 cm), more preferably 0.250–1.250 inches (0.63–3.2 cm) and most preferably 0.50–0.81 inches (1.27–2.1 cm). The sleeve 94 is preferably press-fitted onto the elastomeric coated hub 90. In some embodiments, the elastomeric material is compressed when the sleeve 94 is press-fitted on to the coated hub 90. The interference of the press-fit is dependent upon the embodiment. Preferably, the interference for embossing is about 0.006" (about 0.015 cm). The complexity assembled roll then undergoes a final grind, setting the concentricity of the roll to within about 0.001" (about 0.0025 cm). The sleeve 94 distributes the force of the embosser assembly 50 evenly across the elastomeric intermediate 92.

The intermediate layer 92 (e.g. the elastomeric material) can be molded in different shapes creating spaces or relieved areas 96 to provide different levels of compliance or absorption of stress. One embodiment of the shape of the intermediate layer 92 is shown in detail in FIG. 6. The relieved areas 96 provide discontinuities in the intermediate layer 92 that are perpendicular to the anvil shaft 55. In other embodiments, the discontinuities can be parallel to the anvil shaft 55. Numerous other orientations (e.g. diagonal) are possible. The discontinuities in the intermediate layer 92 provide the anvil roll with increased ability to absorb stresses by giving the elastomeric material an area to flow into when compressive forces are generated during the embossing process. This provides better compliance (ability to yield under compression) without exceeding the ability of the elastomeric material to absorb stresses and not generating excess heat. The unique feature of the anvil roll 54 is that it produces an equal force distribution throughout the roll rotation, which provides several advantages including uniform compliance, low wear, and wide distribution of stress concentrations. This also increases the life of the embossing roll and the reliability of the embosser assembly.

In the preferred embodiment of the anvil roll 54, the layers of the anvil roll 54 are applied concentrically and are open on their ends 57 to allow the materials to flow while under compressive pressure during the embossing process. In an alternate embodiments, the ends 57 of the multi-layered structure may be sealed by extensions of the sleeve 94 joining the hub 90 or the anvil shaft 55.

Other embodiments of the embosser assembly are also possible and are not limited to rolls. For example, an anvil surface and a die surface could be in the form of plates. The anvil roll 54 in FIG. 4 can also have a recessed region 68 having an anvil insert 70 therein. The anvil insert 70 is preferably provided with a pair of bolt holes 72 and is bolted to the anvil roll 54 so that is is preferably also removable. The anvil insert 70 has a substantially smooth surface and is fit into the recessed region 68 of the anvil roll 54. The anvil insert 70 is preferably softer than the remaining portions of the surface of the anvil roll 54 so that the raised portions 62 on the embossing member 60 do not rupture the garment facing side of the sanitary napkin 20.

Various alternative uses for the compliant anvil are possible. Another use for a compliant anvil include cutting operations anywhere in a process for making an absorbent article. The multi-layered system of the compliant anvil reduces stresses and wear to increase the cutting life of the final or initial knife. The anvil can also be used when bonding discrete parts of a web in diapers and catamenial product manufacturing. For example, the anvil can be used in a method of dynamically bonding a laminate between a pair of rolls having a surface velocity differential therebetween described in U.S. Pat. No. 4,854,984 issued to Ball, et al. on Aug. 8, 1989.

In addition, in other embodiments the components of the sanitary napkin may be assembled in a variety of different configurations known in the art and embossed using the method and apparatus of the present invention. Several preferred sanitary napkin configurations are described generally in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. Nos. 4,950,264 and 5,009,653, both entitled "Thin, Flexible Sanitary Napkin" issued to Osborn on Aug. 21, 1990 and Apr. 23, 1991, respectively; U.S. Pat. Nos. B1 4,589,876, 4,687,478, and 5,267,992 issued to Van Tilburg which disclose sanitary napkins having flaps, and the aforementioned patent applications issued to Sneller, et al.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:
1. An embosser assembly for forming a pattern of embossments in an absorbent article, said embosser assembly comprising:
   A.) a die roll; and
   B.) an anvil roll aligned with said die roll, said anvil roll having a multi-layered configuration, and comprising i. a shaft;
ii. a hub;
iii. a compressible layer; and
iv. a sleeve;

said anvil roll providing an anvil surface against which a components of an absorbent article are placed, said anvil shaft having substantially encircled by said hub, said hub being substantially encircled by at least one compressible layer, said compressible layer comprising a discontinuous layer of compressible material, said discontinuous layer of compressible material being disposed around the entire circumference of said hub, said compressible material having open spaces therein, said open spaces being free of intervening material so that when said compressible layer is compressed, said compressible material will move into said open spaces, said compressible layer being substantially enclosed by said sleeve, and C.) a mechanism for applying compressive pressure on the components of an absorbent article when said components are passed through said embosser assembly between said die roll and said anvil roll, wherein said mechanism aligns said anvil roll and said die roll.

2. The apparatus of claim 1 wherein said die roll is patterned.

3. The apparatus of claim 1 wherein said discontinuous layer is oriented perpendicular to said anvil shaft.

4. The apparatus of claim 1 wherein said discontinuous layer is oriented parallel to said anvil shaft.

5. The apparatus of claim 1 wherein said discontinuous layer is oriented diagonal to said anvil shaft.

6. The apparatus of claim 1 wherein said compressible layer comprises a polymer layer.

7. The apparatus of claim 6 wherein said polymer layer comprises an elastomeric material.

8. The apparatus of claim 1 wherein said compressible layer is about 0.25–0.50 inches thick.

9. The apparatus of claim 1 wherein said sleeve comprises a hardened metal material.

10. An anvil roll for use in an embossing assembly for forming a pattern of embossments in an absorbent article, said anvil roll comprising a multi-layered structure;

i. a hub;
ii. a discontinuous layer of compressible material; and
iii. a sleeve wherein said hub is encircled by said discontinuous layer of compressible material, and said discontinuous layer of compressible material substantially enclosed by said sleeve.

* * * * *